(12) United States Patent
Eshel

(10) Patent No.: US 6,270,053 B1
(45) Date of Patent: Aug. 7, 2001

(54) CATHETER VALVE

(75) Inventor: Uzi Eshel, Herzliya (IL)

(73) Assignee: Eumedicaltech, Ltd., Herzliya (IL)

( * ) Notice: Subject to any disclaimer, the term of this patent is extended or adjusted under 35 U.S.C. 154(b) by 0 days.

(21) Appl. No.: 09/536,604

(22) Filed: Mar. 28, 2000

(51) Int. Cl.[7] ............... A61F 5/44; F16K 7/04; F16K 35/02

(52) U.S. Cl. ............... 251/4; 251/96; 604/248; 604/349

(58) Field of Search ............ 251/4, 96, 341, 251/342, 343, 344, 345; 604/32, 34, 248, 250, 349

(56) References Cited

U.S. PATENT DOCUMENTS

| | | | |
|---|---|---|---|
| 2,844,351 | * | 7/1958 | Smith ............... 251/4 |
| 3,739,783 | * | 6/1973 | Broerman ............... 604/349 X |
| 4,292,969 | * | 10/1981 | Raible et al. ............... 251/4 X |
| 5,112,324 | * | 5/1992 | Wallace ............... 604/349 |
| 5,158,553 | * | 10/1992 | Berry et al. ............... 604/248 |
| 5,464,189 | * | 11/1995 | Li ............... 251/4 |

* cited by examiner

*Primary Examiner*—Kevin Shaver
*Assistant Examiner*—Eric Keasel

(57) ABSTRACT

A catheter valve including a housing engaging at least a portion of a tubular member is provided. The tubular member having distal and proximal open ends defining a flow-through passage therebetween, the tubular member further having a proximal portion of a deformable and therefore twistable structure and a distal portion of a more rigid structure, the proximal portion being partially and circumferencially attached to an inner surface of the housing, wherein dimensions of the housing, of the proximal portion and of the distal portion are selected such that when the distal portion is rotated, the proximal portion is twisted so as to block passage of fluid through the tubular member and therefore through the catheter valve and the distal portion is secured by the housing so as to prevent self untwisting of the proximal portion.

9 Claims, 5 Drawing Sheets

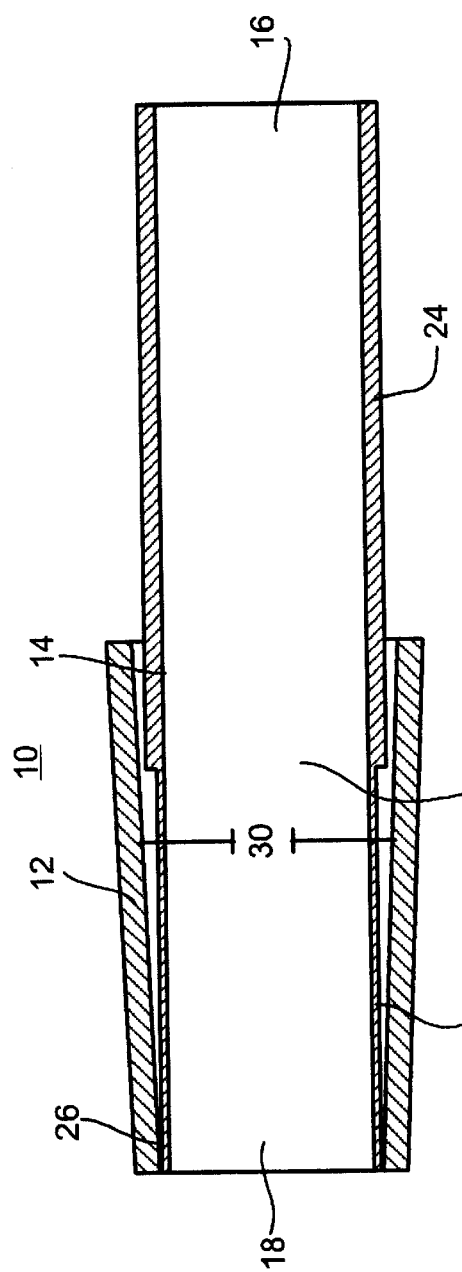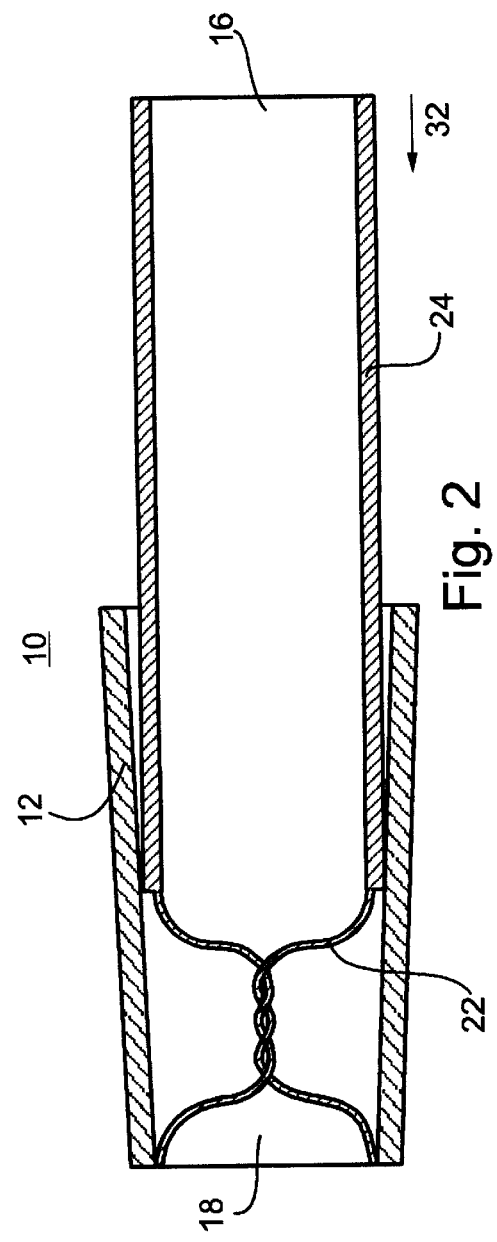

CATHETER VALVE

FIELD AND BACKGROUND OF THE INVENTION

The present invention relates to a catheter valve and, more particularly, to a catheter valve of a mechanically simple design which can be attached to, or integrated into, a urinary catheter, for providing self control over urine outflow.

Catheter valves are well known in the art and a great number of configurations are commercially available as either catheter integral, or catheter plug-in, valves.

The valves employed by urinary catheters, such as for example, drainage catheters, incontinence catheters or other indwelling catheters are typically positioned out of the body so as to allow an individual to control urine outflow from the catheter.

The function and extra-body placement of such urinary catheter valves necessitates that the valve is ergonomically shaped and of small size, such that it does not cause any discomfort or physical damage to a patient even in cases where a patient is confined to a bed for a long time as is the case with older patients. In addition, since the motor functions of older patients are often reduced, a catheter valve must be extremely simple and easy to operate. Finally, in cases of long-term use, the valve must be configured so as to minimize the risk of contamination and therefore infection to the patient.

A number of urinary catheter valves which attempt to meet these requirements have been described in the prior art.

For example, U.S. Pat. No. 4,570,898 describes a catheter and closure device in the form of a valve which remains in place at the drainage funnel of a catheter during normal urination and has to be separated from the funnel only for flushing out. The catheter valve includes a conical part serving for the insertion into the drainage funnel. Additionally, the valve includes on its inside a rubber-elastic valve hose adapted to be influenced from the outside, which during actuation of the valve is opened uninterruptedly but is closed in the non-actuated rest position by a single or multiple kink, fold or twist. The valve includes a fixed part with a through-bore as well as the rubber-elastic hose in extension of this bore. A sleeve with a spring is placed over these parts, whereby the kinked hose is straightened out by the axial displacement of the sleeve opposite the spring force.

U.S. Pat. No. 5,522,806 describes a self-closing catheter valve having a housing with an oval cross section and a conical hose attachment connector which can be inserted into a catheter drainage funnel. A valve hose piece partially extends through the housing. A V-shaped spring element deforms and constricts the valve hose piece by pressing the valve hose piece against a wall of the housing. An actuation member is positioned within the housing for bringing the self-closing catheter valve into an open position.

Although the above described catheter valves substantially improve comfort and ease of operation over other prior art valves, they are inherently limited by a mechanically complex configuration which utilizes spring elements for retaining a closed position. In addition, since such valves are designed to self close, an individual must physically maintain an open position to allow urine outflow, thus increasing the risk of valve contamination and therefore infection and severely limiting ease of operation.

There is thus a widely recognized need for, and it would be highly advantageous to have, a catheter valve which is mechanically simple and ergonomic and which can be operated with ease even by older patients with reduced motor functions.

SUMMARY OF THE INVENTION

According to one aspect of the present invention there is provided a catheter valve comprising a housing engaging at least a portion of a tubular member, the tubular member having distal and proximal open ends defining a flow-through passage therebetween, the tubular member further having a proximal portion of a deformable and therefore twistable structure and a distal portion of a more rigid structure, the proximal portion being partially and circumferencially attached to an inner surface of the housing, wherein dimensions of the housing, of the proximal portion and of the distal portion are selected such that when the distal portion is rotated, the proximal portion is twisted so as to block passage of fluid through the tubular member and therefore through the catheter valve and the distal portion is secured by the housing so as to prevent self untwisting of the proximal portion.

According to another aspect of the present invention there is provided a method of controlling urine outflow from a urinary catheter, the method comprising the steps of: (a) attaching a catheter valve to a distal portion of the urinary catheter, the catheter valve including a housing engaging at least a portion of a tubular member, the tubular member having distal and proximal open ends defining a flow-through passage therebetween, the tubular member further having a proximal portion of a deformable and therefore twistable structure and a distal portion of a more rigid structure, the proximal portion being partially and circumferencially attached to an inner surface of the housing; (b) rotating the distal portion so as to twist the proximal portion to thereby block passage of fluid through the tubular member and therefore through the catheter valve; and (c) securing the distal portion within the housing so as to prevent self untwisting of the proximal portion.

According to further features in preferred embodiments of the invention described below, the housing is of a tapering inner cross section, and as such step (c) is effected by translation of the distal portion within the housing in a proximal direction during or following rotation thereof.

According to still further features in the described preferred embodiments the proximal and distal portions of the tubular member are formed from a single material of variable thickness, whereas the proximal portion is thinner than the distal portion.

According to still further features in the described preferred embodiments the proximal and distal portions of the tubular member are formed from different materials wherein a Shore value of the proximal portion is lower than a Shore value of the distal portion.

According to still further features in the described preferred embodiments the housing is of a tubular shape.

According to still further features in the described preferred embodiments following twisting of the proximal portion, the distal portion is secured in the housing via frictional forces.

According to still further features in the described preferred embodiments the housing of the catheter valve is configured so as to be attachable to a drainage funnel of a urinary catheter.

According to still further features in the described preferred embodiments the distal portion is rotated at least 180 degrees relative to the housing.

According to still further features in the described preferred embodiments the housing is of a tapering inner cross section, such that translation of the distal portion within the housing in a proximal direction during or following rotation thereof secures the distal portion within the housing so as to prevent untwisting of the proximal portion.

According to still further features in the described preferred embodiments there is provided a urinary catheter comprising the catheter valve described herein.

According to still further features in the described preferred embodiments the catheter valve forms an integral part of the urinary catheter.

According to another aspect of the present invention, there is provided a catheter valve comprising a tubular element being engaged within a tubular housing, the tubular element and the tubular housing being designed and constructed so as to restrict flow through the catheter valve when the tubular element is twisted relative to the tubular housing and to allow flow through the catheter valve when the tubular element is at least partially pulled out of the tubular housing.

The present invention successfully addresses the shortcomings of the presently known configurations by providing a catheter valve of a simple mechanical design which is simple to operate even by individuals with reduced motor functions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a cross sectional view of an open catheter valve according to the teachings of the present invention;

FIG. 2 is a cross sectional view of a closed catheter valve according to the teachings of the present invention;

DESCRIPTION OF THE PREFERRED EMBODIMENTS

Figure 3:
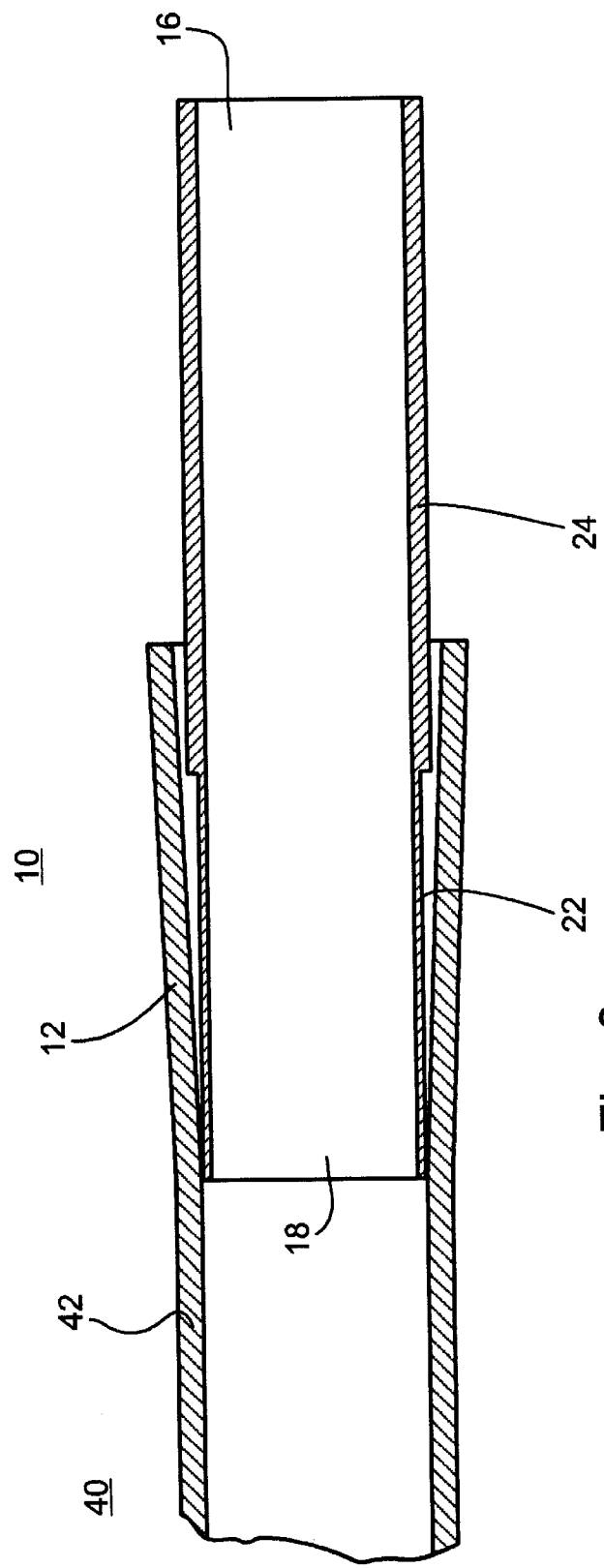
FIG. 3 is a is a cross sectional view of an open catheter valve according to the teachings of the present invention integrated with a urinary catheter.

The present invention is of a catheter valve which can be attached to, or integrated with a urinary catheter and which can be easily actuated between open and closed positions thus providing control over urine outflow even in individuals with reduced motor functions. In addition, the catheter valve of the present invention is configured such that when utilized by urinary catheters, it limits both discomfort and chances of contamination, while greatly facilitating control over urine outflow.

The principles and operation of a catheter valve according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein the terms "distal" or "distally" refer to a direction away from a patient's body wherein the terms "proximal" or "proximally" refer to the opposite direction.

Referring now to the drawings, FIGS. 1–7 illustrate the catheter valve of the present invention which is referred to herein as valve 10. Valve 10 is preferably attached to, or integrated with urinary catheters such as drainage catheters, incontinence catheters or other indwelling catheters.

Valve 10 includes a housing 12 which engages at least a portion of a tubular member 14. Housing 12 is preferably tubular in shape and is composed of a material such as silicon rubber, polyurethane, polyvinylchloride, polypropylene, latex and the like which supports a structure. It will be appreciated that when valve 10 forms a part of a urinary catheter, as specifically shown in FIGS. 3–4, the material of housing 12 is selected so as to not cause discomfort when utilized by a catheter fitted to an individual. On the other hand when valve 10 is a plug-in valve, the material of housing 12 is selected such that valve 10 can be easily inserted and secured in a drainage funnel of a urinary catheter in a manner which prevents leaks.

Tubular member 14 includes distal 16 and proximal 18 open ends defining a flow-through passage 20 therebetween. Tubular member 14 is composed of a proximal portion 22 which is of a deformable and therefore twistable structure and a distal portion 24 of a more rigid structure.

According to one preferred embodiment of the present invention, proximal portion 22 and distal portion 24 are formed from a single material of a variable thickness, in which case proximal portion 22 is thin and therefor deformable, while distal portion 24 is thick and therefor more rigid.

Figure 6:
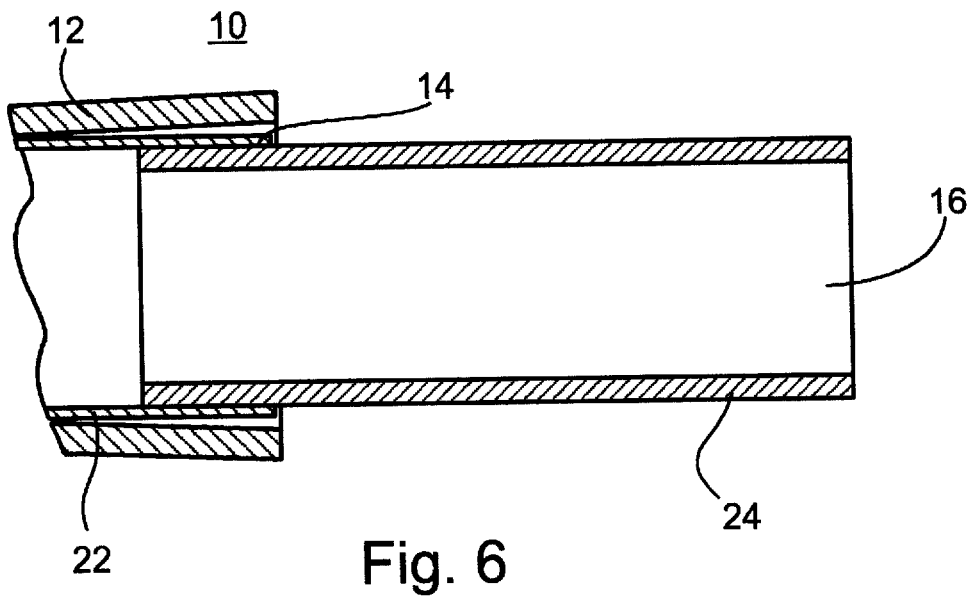
FIG. 6 is a cross sectional view of a catheter valve according to the teachings of the present invention illustrating one configuration of the tubular element of the catheter.
Figure 7:
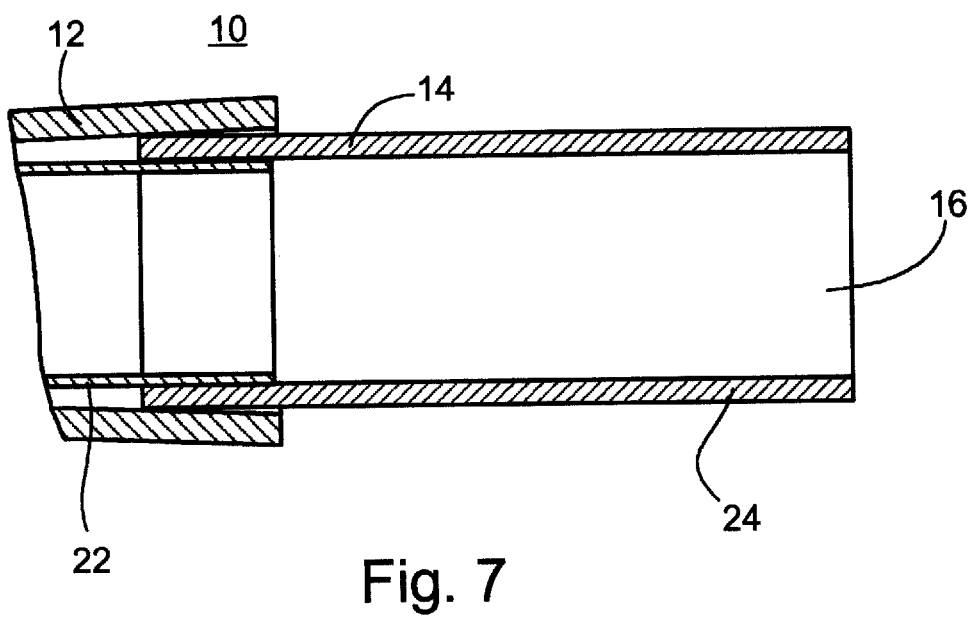
FIG. 7 is a cross sectional view of a catheter valve according to the teachings of the present invention illustrating another configuration of the tubular element of the catheter.

Alternatively, and as shown in FIGS. 6–7 proximal portion 22 and distal portion 24 can be fabricated from different materials of a different Shore A hardness value which are bonded or welded to form tubular member 14. For example, proximal portion 22 can be fabricated from silicon rubber or polyurethane or any material of a 30–50 Shore A hardness value range, while distal portion 24 can be fabricated from a material such as for example silicon rubber or polyurethane, or any material of a 30–90 Shore A hardness value range.

Proximal portion 22 can be bonded or welded to housing 12. Alternatively, and as specifically shown in FIG. 5, when such bonding or welding is difficult or impossible to effect, proximal portion 22 can be mechanically attached to housing 12, by for example pressure disc 38 which pressure locks a protrusion 23 of proximal portion 22 against an inner wall of housing 12.

According to the present invention, when distal portion 24 is rotated about a longitudinal axis of valve 10, proximal portion 22 which is partially and circumferencially attached to an inner surface 26 of housing 12 is twisted around (as is specifically shown in FIG. 2) so as to block passage of fluid through tubular member and therefore through valve 10. Distal portion 24 is rotated at least 180 degrees, preferably more, so as to ensure a leak proof twist or twists in proximal portion 22.

The dimensions of housing 12, of proximal portion 22 and of distal portion 24 are selected such that following rotating, distal portion 24 is secured (e.g. frictionally biased) against an inner surface of housing 12 thus preventing self untwisting of proximal portion 22 and accidental flow-through from valve 10.

According to a preferred embodiment of the present invention, the inner cross section 30 of housing 12 tapers towards proximal end 18. As such when distal portion 24 is rotated and proximal portion 22 twists and therefor shortens, distal portion 24 is translated in the proximal direction, as indicated by 32, and wedged within housing 12. This secures distal portion 24 within housing and prevents untwisting of proximal portion 22. Preferably, distal portion 24 is further manually translated in the proximal direction so as to more tightly wedge and secure distal portion 24 within housing 12. To open valve 10, a user simply temporary pulls on distal portion 24 opposite to direction 32, so as to unbias and release distal portion 24 from housing 12 thus allowing twisted proximal portion 22 which is preferably of a material and shape having a memory to self unwind to thereby allow flow through tubular member 14 and therefore through valve 10. It will be appreciated that self unwinding of proximal portion 22 may be further assisted by an internal fluid pressure.

This flow-through control mechanism of valve 10 of the present invention is particularly advantageous since it is mechanically simple and therefor inexpensive to manufacture. In addition, such control mechanism can be easily and blindly actuated between closed or opened positions even by individuals with reduced motor functions such as elderly individuals.

It will be appreciated that housing 12 and/or distal portion 24 can alternatively or additionally include a locking mechanism which can be utilized to interlock distal portion 24 and housing 12 following rotation and twisting of proximal portion 22. Such mechanisms can include, for example, inter-lockable protrusions and notches or any other mechanism formed of interlocking elements which can be attached to or integrally formed with distal portion 24 and housing 12.

Figure 4:
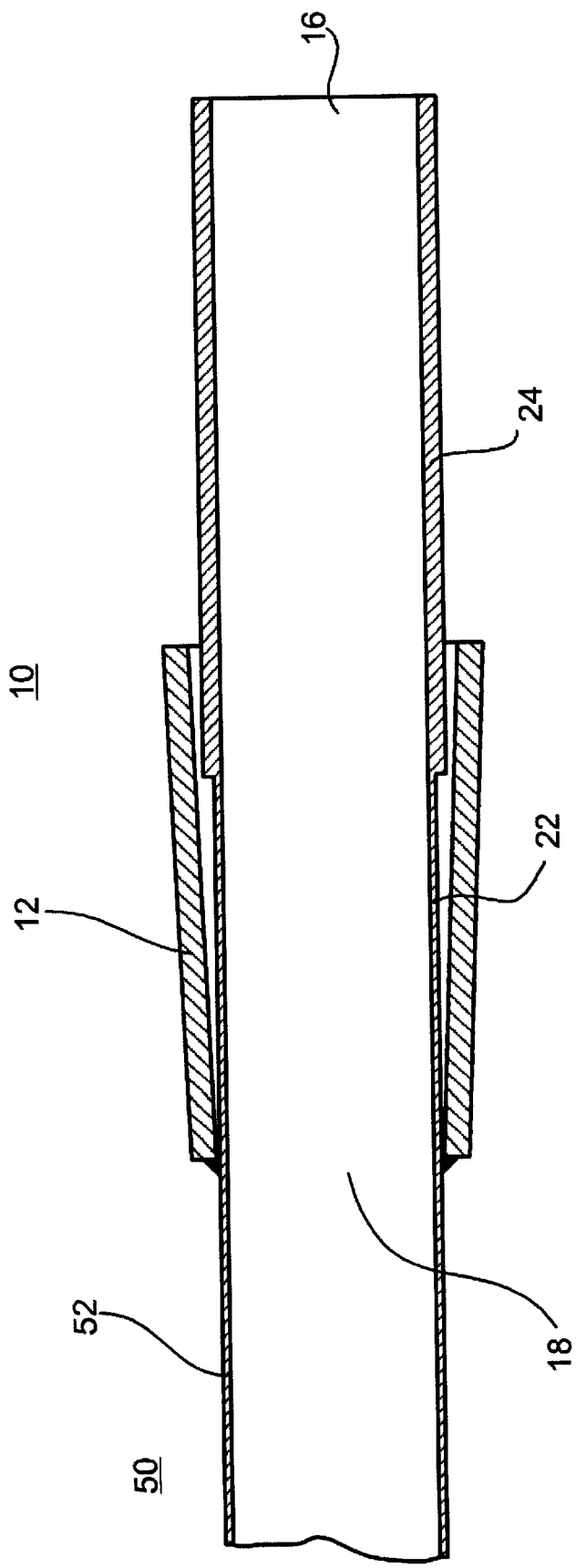
FIG. 4 is a is a cross sectional view of an open catheter valve according to the teachings of the present invention integrated with a thin walled urinary catheter.

According to another preferred embodiments of the present invention and as shown in FIGS. 3–4 valve 10 forms an integral part of a catheter.

As specifically shown in FIG. 3, when catheter 40 is a thick-walled catheter, housing 12 of valve 10 is an extension of a body 42 of catheter 40. As specifically shown in FIG. 4, and in the case of a thin-walled catheters, proximal portion 22 is an extension of body 52 of catheter 50.

Catheters 40 and 50 can be any type of urinary catheters including incontinence catheters, drainage catheters and retention catheters.

Figure 5:
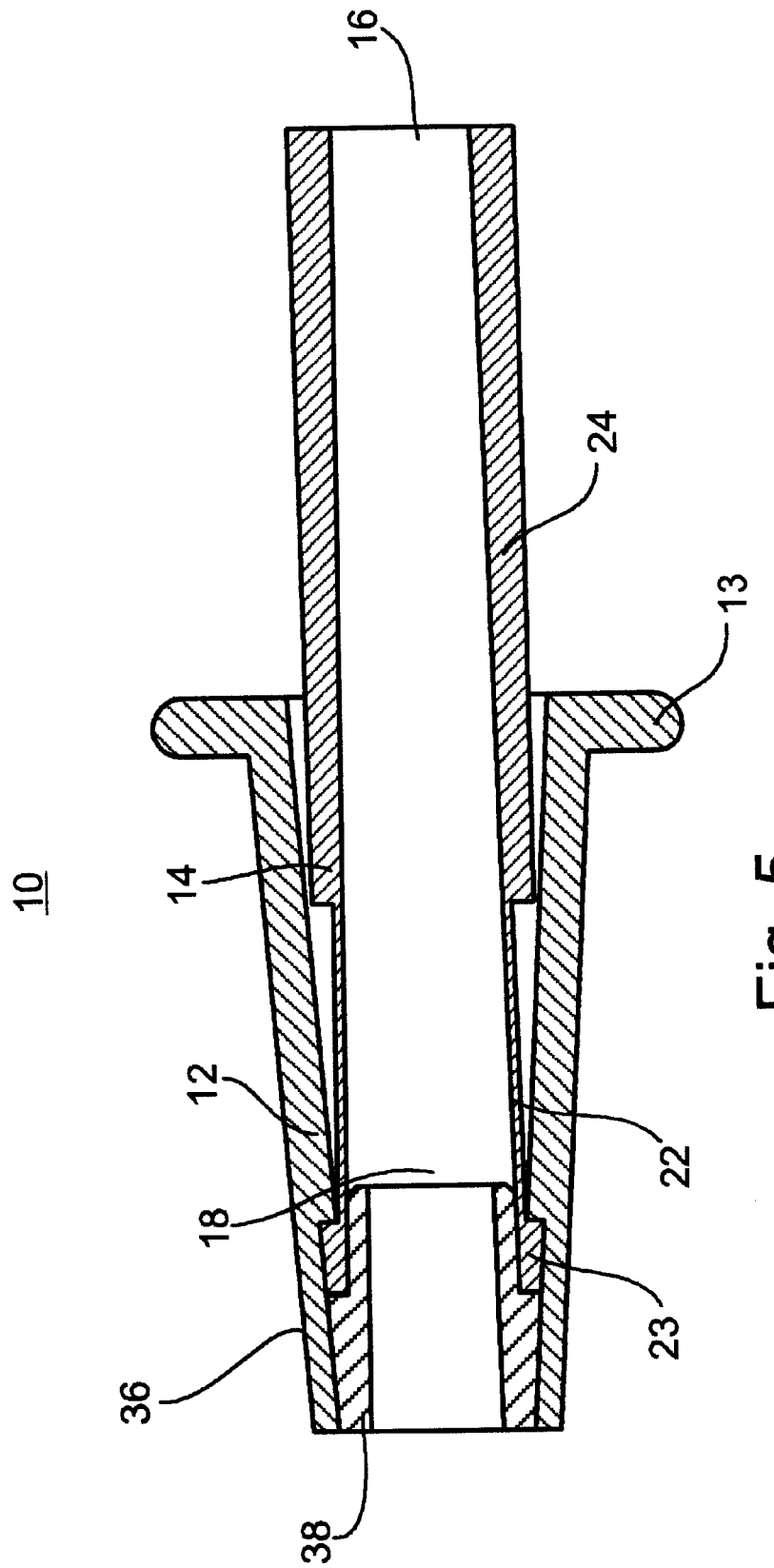
FIG. 5 is a cross sectional view of a plug-in configuration of a catheter valve according to the teachings of the present invention.

According to another preferred embodiment of the present invention and as specifically shown in FIG. 5, valve 10 is a plug-in catheter valve which can be plugged into a drainage funnel of a urinary catheter. Thus, in this case housing 12 is shaped with a tapered region 36 which serves to facilitate insertion of valve 10 into the drainage funnel of a urinary catheter. Once inserted into the drainage funnel, housing 12 is tightly held in place by frictional forces. Valve 10 according to this embodiment can also include a protrusion 13 attached to or integrally formed with housing 12. Preferably, protrusion 13 extends from an outer diameter of a distal end of housing 12. Protrusion 13 serves as finger holds for forcing valve 10 into, or out of, the drainage funnel.

The catheter valve of the present invention traverses limitations inherent to prior art catheter valves. It is mechanically simple and therefor not subjected to wear induced leakage or other malfunctions. In addition, it is small and therefor unobtrusive and as such does not cause patient discomfort when positioned. Finally, it is extremely easy to operate through open (flow-through) and closed positions thus enabling individuals with limited or reduced motor functions which are fitted with a urinary catheter utilizing the catheter valve of the present invention control over urine outflow.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this application shall not be construed as an admission that such reference is available as prior art to the present invention.

What is claimed is:

1. A catheter valve comprising a housing engaging at least a portion of a tubular member, said tubular member having distal and proximal open ends defining a flow-through passage therebetween, said tubular member further having a proximal portion of a deformable and therefore twistable structure and a distal portion of a more rigid structure, said proximal portion being partially and circumferencially attached to an inner surface of said housing, wherein dimensions of said housing, of said proximal portion and of said distal portion are selected such that when said distal portion is rotated, said proximal portion is twisted so as to block passage of fluid through said tubular member and therefore through the catheter valve and said distal portion is frictionally engaged by an inner surface of said housing thus preventing self untwisting of said proximal portion, wherein pulling of said distal portion in a direction away from said housing disengages said distal portion from said inner surface of said housing thereby allowing self untwisting of said proximal portion and passage of fluid through said tubular member.

2. The catheter valve of claim 1, wherein said proximal and distal portions of said tubular member are formed from a single material of varible thickness, whereas said proximal portion is thinner than said distal portion.

3. The catheter valve of claim 1, wherein said proximal and distal portions of said tubular member are formed from different materials wherein a Shore valve of said proximal portion is lower than a Shore value of said distal portions.

4. The catheter valve of claim 1, wherein said housing is of a tubular shape.

5. The catheter valve of claim 1, wherein said housing of the catheter valve is configured so as to be attachable to a drainage funnel of a urinary catheter.

6. The catheter of claim 1, wherein said distal portion is rotated at least 180 degrees relative to said housing.

7. The catheter of claim 1, wherein said housing is of a tapering inner cross section, such that translation of said distal portion within said housing in a proximal direction during or following rotation thereof secures said distal portion within said housing so as to prevent untwisting of said proximal portion.

8. A urinary catheter comprising the catheter valve of claim 1.

9. The urinary catheter of claim 8, wherein the catheter valve forms an integral part of the urinary catheter.

* * * * *